(12) United States Patent
Hastings

(10) Patent No.: US 8,496,979 B1
(45) Date of Patent: Jul. 30, 2013

(54) CAFFEINE-FREE DIETARY SUPPLEMENTS FOR INCREASING ENERGY AND METHODS OF ADMINISTERING THE SAME

(75) Inventor: Carl W. Hastings, Wildwood, MO (US)

(73) Assignee: Reliv International, Inc., Chesterfield, MO (US)

( * ) Notice: Subject to any disclaimer, the term of this patent is extended or adjusted under 35 U.S.C. 154(b) by 1 day.

(21) Appl. No.: 13/365,246

(22) Filed: Feb. 2, 2012

(51) Int. Cl.
*A61K 36/84* (2006.01)
*A61K 31/202* (2006.01)
*A61K 31/05* (2006.01)
*A61K 31/195* (2006.01)

(52) U.S. Cl.
USPC ........... 424/733; 514/558; 514/733; 514/734; 514/561

(58) Field of Classification Search
USPC .................. 424/733; 514/558, 561, 733, 734
See application file for complete search history.

(56) References Cited

U.S. PATENT DOCUMENTS

| | | | |
|---|---|---|---|
| 2008/0014331 A1* | 1/2008 | Badalov | 426/658 |
| 2009/0162457 A1* | 6/2009 | Minegishi et al. | 424/766 |
| 2009/0220575 A1* | 9/2009 | Harris et al. | 424/439 |

OTHER PUBLICATIONS

"5-hour Energy® Ingredients & Safety," (2011). Retrieved from the Internet on Dec. 12, 2011: URL:http://www.5hourenergy.com/ingredients.asp.
"How to Use 5-hour Energy® Shots," (2011). Retrieved from the Internet on Dec. 12, 2011: URL:http://www.5houreneregy.com/healthfacts.asp?Product=decaf.
"Ingredient Trends Likely to Help Boost Sales in 2010," *Nutrition Business Journal* (2009).
"SNWL Sales Suffer Blow from Recession and Flurry of Negative News Events; Category Growth Stalls, as Companies Deal with Sluggish Consumer Spending, FDA Warnings and Product Recalls," *Nutrition Business Journal* (Sep. 2009).
American International Chemical, Inc., Specification Sheet, "DL-Choline Bitartrate," Publicly available prior to Feb. 2, 2012.
Chemi Nutra, Technical Data Sheet, "AlphaSize® 50WSP," Publicly available prior to Feb. 2, 2012.
Compound Solutions, Specification Sheet, "CarnoSyn® beta-Alanine," (2010).
Enzymotec Ltd., Technical Data Sheet, "Sharp-PS™ 60P-SF, 60% Powder Phosphatidylserine Soybean Free" Valid From: May 10, 2009.
Ethical Naturals, Inc., Production Specification, "ProfileProven™ Resveratrol (Water Soluble)," Publicly available prior to Feb. 2, 2012.
Frutarom, Certificate of Analysis, "Wild Green Oat Neuravena," Release Date: Sep. 5, 2007.
Glanbia Nutritionals, Raw Material Specification Sheet, "Gamma Amino Butyric Acid (GABA)," Effective Date: Sep. 30, 2009.
Hebei Yuxing Bio-Engineering Co., Ltd., "Vitamin $B_{12}$ USP 32," Publicly available prior to Feb. 2, 2012.

Heckman et al., "Energy Drinks: An Assessment of Their Market Size, Consumer Demographics, Ingredient Profile, Functionality, and Regulations in the United States," *Comprehensive Reviews in Food Science and Food Safety*, 9:303-317 (2010).
Marco Hi-Tech, Product Specification, "Huperzine-A (98.0%-99.0%) PWD," Publicly available prior to Feb. 2, 2012.
Naturex, Production Specification, "Vinca Minor PE 4:1 ," May 26, 2010.
Northeast General Pharmaceutical Factory, Specification, "L-Carnitine Base USP," Publicly available prior to Feb. 2, 2012.
Nutraceuticals, Product Specification, "Blueberry PE 5:1," Revised: Feb. 28, 2010.
Nutraceuticals, Product Specification, "Ginkgo Leaves Extract SD," Supersedes Date: Feb. 4, 2010.
Nutraceuticals, Product Specification, "Valerian Officinalis Root Extract," Revised Date: May 4, 2006.
Nutratech, Specification, "Acetyl L-Carnitine HCL," Revised Date: Jun. 7, 2000.
Nutrition & Health Data Profile, "Omevital™ 30% MP Gold," Publicly available prior to Feb. 2, 2012.
Pharmline Inc., Product Specification, "Grape Seed Extract 95%," Last Modified: Sep. 18, 2009.
Pharmline, Product Specification, "L-Theanine 98% (Synthetic)," Sep. 30, 2010.
Pharmline, Product Specification, "Ubidecarenone (Coenzyme $Q_{10}$)," Apr. 2004.
Premium Ingredients, Ltd., Analytical Specification, "Inositol," Publicly available prior to Feb. 2, 2012.
Qianjiang Yongan Pharmaceutical Co., Ltd., Specification Sheet, "Taurine; CAS:107-35-7," Publicly available prior to Feb. 2, 2012.
"Rebpure, Physical and Organoleptic Standards," Publicly available prior to Feb. 2, 2012.
Roxlor International, Product Sheet, "CitriSweet™," Publicly available prior to Feb. 2, 2012.
Sabinsa Corporation, Certificate of Analysis, "Curcumin C3 Complex®," Manufacturing Date: Jun. 2008.
Serenzo™ Specification Sheet—Ref. 600092, Updated: Mar. 9, 2010.
Sloan, "Getting Ahead of the Curve: Mental Performance & Brain Health," Sloan Trends Inc. (2010).
Tate & Lyle, Specification and Technical Data Sheet, "Malic Acid, FCC," Publicly available prior to Feb. 2, 2012.
Zhejian Tianxin Pharmaceutical Co., Ltd., Specification for Pyridoxine Hydrochloride, Publicly available prior to Feb. 2, 2012.

\* cited by examiner

*Primary Examiner* — Rosanne Kosson
(74) *Attorney, Agent, or Firm* — Marshall, Gerstein & Borun LLP

(57) ABSTRACT

Disclosed herein are caffeine-free dietary supplements for increasing energy in a subject and methods of administering the same. The method comprises administering to a subject a caffeine-free dietary supplement comprising omega-3 fatty acids, resveratrol, beta-alanine, gamma aminobutyric acid, and valerian root extract product, in amounts such that the supplement is effective for increasing energy and mental focus and relieving stress in the subject.

21 Claims, No Drawings

CAFFEINE-FREE DIETARY SUPPLEMENTS FOR INCREASING ENERGY AND METHODS OF ADMINISTERING THE SAME

FIELD OF THE INVENTION

The invention relates to caffeine-free dietary supplements for increasing energy and methods of administering the same.

BACKGROUND OF THE INVENTION

The energy drink market is a fast-growing sector of the beverage industry. Individually packaged energy drinks typically containing one to three ounces of a concentrated formula are often referred to as "energy shots." Energy shots are popular among consumers who desire energy drinks that are convenient to transport and consume. Energy shots are small enough to easily carry throughout the day and do not require refrigeration, so they are compatible with the increasingly busy lifestyle of the average consumer.

The majority of the energy drinks on the market rely on stimulants such as caffeine and sugar to provide a feeling of increased energy. Such ingredients only temporarily treat fatigue, however, and are known to have negative side effects.

For example, caffeine is a drug that stimulates the central nervous system, heart, muscles, and blood pressure control centers, providing an artificial lift which simulates an increase in energy. Caffeine inhibits the activity of the neuroprotective agent adenosine to mask fatigue. After a few hours, there is an inevitable "crash" that sets in after the effects of caffeine diminish, wherein one is left feeling sluggish and even more exhausted than before. Further, excessive caffeine can result in a number of unwanted side effects including, for example, anxiety, nausea, and high blood pressure. Habitual consumption of caffeine can also lead to addiction withdrawal symptoms including fatigue, depression, and decreased mental alertness. Indeed, the health risks of caffeine have prompted several countries to ban energy drinks containing the drug.

In addition to caffeine, energy drinks typically contain large amounts of simple carbohydrates, usually in the form of high fructose corn syrup and other refined sugars. Simple carbohydrates are rapidly digested and absorbed by the body. The surge in blood sugar from high-carbohydrate energy drinks triggers insulin secretion, which subsequently reduces blood sugar levels. The resulting decrease in blood sugar, known as reactive hypoglycemia, can cause physical weakness, confusion, and nervousness. Additionally, excessive sugar and the accompanying calories can lead to health problems including obesity, heart disease, and diabetes.

As a lower-calorie option, some energy drinks are sugar-free and instead include sugar substitutes. Energy drinks that are sugar-free typically contain artificial sweeteners such as, for example, acesulfame potassium, aspartame, neotame, saccharin, and sucralose. Artificial sweeteners can cause digestive problems and other health issues, particularly in those with a sensitivity to sugar substitutes. A frequently used artificial sweetener is sucralose, a chlorinated sugar substitute. Reported side effects from sucralose consumption include migraines, weight gain, and stomach pain. Additionally, some artificial sweeteners have been shown to cause cancer in laboratory studies.

Besides caffeine and sugar, many energy shots currently on the market also rely on 25 milligrams or more of niacin, based on the total weight of the dietary supplement per serving, to provide energy. The Food and Nutrition Board of the Institute of Medicine has set a recommended daily allowance of 14-16 milligrams for niacin, which is also known as Vitamin B3. Niacin can be found in, for example, meat, vegetables, and nuts, and the recommended daily amount can be readily achieved through diet alone. While increasing energy, doses of niacin above the recommended amount, in particular, supplementation of 25 milligrams or more over a 24-hour period, frequently cause side effects. A common side effect is a reaction known as a "niacin flush" which is characterized by unsightly reddening of the skin and painful burning sensations on the face and chest. Other side effects from niacin include dizziness and stomach pains.

The leading energy shot product, which claims to provide energy for five hours, contains over 200 milligrams of caffeine and 30 milligrams of niacin per serving among its active ingredients. The product label contains a warning that caffeine products may cause nervousness, sleeplessness, and rapid heartbeat. Because the niacin from the supplement is considerably more than the recommended daily amount, the product label also warns that consumers may experience a niacin flush. The leading product also contains the artificial sweetener sucralose.

In addition to the negative effects of excessive caffeine, niacin, sugar, and artificial sweeteners, current leading energy drinks offer few benefits beyond a temporary artificial feeling of increased energy and do not address the underlying causes of fatigue.

SUMMARY OF THE INVENTION

The disclosed caffeine-free dietary supplements and methods of administering the same can advantageously be used to treat subjects who desire increased energy, improved mental focus, and/or stress relief by actually addressing the underlying causes of fatigue In one aspect, a caffeine-free dietary supplement for increasing energy in a subject comprises omega-3 fatty acids, resveratrol, beta alanine, gamma aminobutyric acid (GABA), and valerian root extract product, in amounts such that the supplement is effective for increasing energy and mental focus and reducing stress. In a refinement, the caffeine-free dietary supplement further comprises B vitamins (in particular, Vitamins B6 and B12) and coenzyme Q10.

In a related aspect, a method for increasing energy in a subject comprises administering to a subject a caffeine-free dietary supplement comprising omega-3 fatty acids, resveratrol, beta alanine, GABA and valerian root extract product, in amounts such that the supplement is effective for increasing energy and mental focus and reducing stress in the subject. In a refinement, the method comprises administering a caffeine-free dietary supplement that further comprises B vitamins (in particular, Vitamins B6 and B12) and coenzyme Q10.

DETAILED DESCRIPTION OF THE INVENTION

The invention provides caffeine-free dietary supplements for increasing energy in a subject and methods of administering the same. The dietary supplements of the invention comprise omega-3 fatty acids, resveratrol, beta alanine, GABA and valerian root extract product in amounts such that the supplements are effective for increasing energy and mental focus and reducing stress in a subject. In a refinement, the dietary supplements may further include B vitamins (in particular, Vitamins B6 and B12) and coenzyme Q10.

Advantageously, the dietary supplements of the invention provide energy by combating the three factors that the inventors found contribute to a lack of energy: physical fatigue, mental fog, and stress. Physical fatigue can stem from a low rate of metabolism and lack of muscle tone. The slow cellular activity associated with physical fatigue can also hobble the brain and nervous system, causing mental fog. Physical fatigue and mental fog result in poor performances in daily activities and thereby increase stress. Stress in turn burdens the body's systems and exacerbates both physical fatigue and mental fog. Physical fatigue, mental fog, and increased stress levels therefore form a self-perpetuating cycle that drains energy. Energy drinks currently on the market may superficially target one of the factors contributing to a lack in energy to create a transient artificial lift, but do not correct the underlying imbalances to meaningfully and purposefully improve energy and mental focus and reduce stress levels.

The dietary supplements comprise a combination of active ingredients that act synergistically to provide a natural and healthy source of energy. The dietary supplements include active ingredients that play critical roles in metabolism and the generation of energy within the cells of the body to alleviate physical fatigue. The dietary supplements also support the production of neutrotransmitters and protect brain cells to achieve optimal brain functioning and improve mental focus. Unlike other energy drinks, which can cause mood swings and restlessness, the dietary supplements of the invention quiet nervous brain and muscle activity to provide stress relief. Beneficially, the dietary supplements of the invention do not rely on stimulants such as caffeine and sugar to temporarily mask symptoms of fatigue and therefore avoid the negative effects of such ingredients.

Indeed, the dietary supplements of the invention are unexpectedly effective for increasing energy without caffeine, an ingredient commonly used in energy shots. The majority of energy shot products currently on the market contains 100 to 500 milligrams of caffeine per serving. In contrast, the dietary supplements of the invention are substantially free of caffeine. In the context of this invention, "substantially free of caffeine" means that the dietary supplements contain less than about 10 milligrams of caffeine per serving. More preferably, the dietary supplements of the invention contain less than about 5 milligrams and most preferably less than about 1 milligram, for example, 0 milligrams of caffeine per serving. As used herein, in the context of this invention, a "serving" refers to a dietary supplement according to the invention formulated as one fluid ounce.

Additionally, the dietary supplements of the invention are low in sugar and therefore do not cause a surge in blood sugar and subsequent crashing feeling. Many energy shots contain high levels, i.e., more than 3000 milligrams per serving, of simple sugars to provide energy. The dietary supplements according to the invention may include natural sweetening agents including complex sugars such as oligofructose and/or extracts from the Stevia plant, such as rebiana (rebaudioside A). When the dietary supplements of the invention are administered in a serving size of about one fluid ounce, the dietary supplements typically include between about 20 milligrams to about 500 milligrams, and/or between about 100 milligrams to about 400 milligrams, for example, about 120 milligrams to about 250 milligrams of natural sweetening agents. Examples of suitable commercially available natural sweetening agents include Citrisweet® (Roxlor International) and Rebpure™ (GLG Life Tech Corporation).

Despite being low in sugar, the dietary supplements of the invention are substantially free of artificial sweeteners and thereby avoid the health risks associated with their use. In the context of this invention, "substantially free of artificial sweeteners" means the dietary supplements contain less than about 1 wt % of artificial sweeteners, based on the total weight of the composition. More preferably, the dietary supplements contain less than about 0.5 wt %, and most preferably less than about 0.1 wt %, for example, 0 wt % of artificial sweeteners, based on the total weight of the dietary supplement. Although the dietary supplements of the invention are substantially free of artificial sweeteners, the supplements are still low in calories and carbohydrates. The dietary supplements of the invention generally include less than about 10 calories, and/or less than about 7 calories, for example, about 5 calories per serving. The dietary supplements of the invention generally include less than about 2 grams, and/or less than about 1.5 grams, for example, about 1 gram of total carbohydrates per serving.

In addition to being substantially free of caffeine and low in sugar, the dietary supplements of the invention advantageously will not cause side effects associated with overconsumption of niacin, which can be expected with many leading energy shot products. In one aspect, the dietary supplements of the invention are substantially free of niacin. The term "substantially free of niacin" means that the dietary supplements contain less than about 10 milligrams of niacin per serving. More preferably, the dietary supplements contain less than about 5 milligrams, and most preferably, less than about 1 milligram, for example, 0 milligrams of niacin per serving.

The dietary supplements of the invention include omega-3 fatty acids. Omega-3 fatty acids are essential fatty acids that cannot be synthesized by the body. Omega-3 fatty acids stimulate blood circulation and aid in energy production. Omega-3 fatty acids are instrumental in the development and function of brain cells and can help improve mental focus, learning and memory. For example, omega-3 fatty acids make cell membranes more fluid, thereby improving communication between brain cells. Omega-3 fatty acids can also ease feelings of depression or anxiety. Examples of omega-3 fatty acids include, but are not limited to, $\alpha$-linolenic acid, stearidonic acid, eicosatrienoic acid, eicosatetraenoic acid, eicosapentaenoic acid (EPA), docosahexaenoic acid (DHA), docosapentaenoic acid, tetracosapentaenoic acid, and tetracosahexaenoic acid. Omega-3 fatty acids can be derived from, for example, algae, fish oils, flaxseed, nuts, and vegetable oils. EPA and DHA are generally preferred. The dietary supplements of the invention generally include between about 0.01 wt % to about 5 wt %, between about 0.05 wt % to about 2 wt %, for example, about 0.075 wt. % to about 0.4 wt % of omega-3 fatty acids, based on the total weight of the dietary supplement. Typically, the dietary supplements of the invention are administered in a serving size of about one fluid ounce. When the dietary supplements are administered in a serving size of one fluid ounce, the dietary supplements typically include between about 5 milligrams to about 1000 milligrams, about 10 milligrams to about 200 milligrams, and/or between about 15 milligrams to about 125 milligrams, for example, about 20 milligrams to about 100 milligrams of omega-3 fatty acids, in particular EPA and DHA. A suitable commercially available source of omega-3 fatty acids is Omevital™ (BASF).

The dietary supplements of the invention include resveratrol. Resveratrol is an antioxidant that boosts energy and helps muscles use oxygen more efficiently to improve physical performance and endurance. Resveratrol combats mental fog by improving blood flow to the brain to enhance brain performance and focus. Resveratrol also has neuroprotective effects that preserve optimal brain function. Reserveratrol can be extracted from, for example, grapes, mulberries, peanuts, and plants in the *Polygonum* genus, including knotweed, and is commercially available as a dietary supplement. The dietary supplements of the invention generally include between about 0.001 wt % to about 1 wt %, and/or between about 0.005 wt % to about 0.5 wt %, for example, about 0.0075 wt % to about 0.01 wt % of resveratrol, based on the total weight of the dietary supplement. When the dietary supplements of the invention are administered in a serving size of about one fluid ounce, the dietary supplements typically include between about 0.1 milligrams to about 250 milligrams, about 0.5 milligrams to about 100 milligrams, and/or between about 1 milligram to about 50 milligrams, for example, about 2 milligrams to about 5 milligrams of resveratrol.

The dietary supplements of the invention include beta alanine. Beta alanine is a naturally occurring amino acid that supports the production of carnosine to reduce physical fatigue. Carnosine is a peptide that improves muscle strength and endurance. The dietary supplements may include between about 0.1 wt % to about 10 wt %, and/or between about 0.25 wt % to about 5 wt %, for example, about 0.50 wt % to about 1.50 wt % of beta alanine, based on the total weight of the dietary supplement. When the dietary supplements of the invention are administered in a serving size of about one fluid ounce, the dietary supplements typically include between about 25 milligrams to about 3000 milligrams, about 50 milligrams to about 1000 milligrams, and/or between about 100 milligrams to about 500 milligrams, for example, about 200 milligrams to about 400 milligrams of beta alanine. A suitable commercially available beta alanine supplement is Carnosyn® (Natural Alternatives International, Inc.).

The dietary supplements of the invention include gamma aminobutyric acid (GABA). GABA is an inhibitory neurotransmitter that regulates nerve activity to create a sense of calm. GABA decreases electrical activity and nerve impulses in the brain, which reduces anxiety. GABA also increases endorphins and regulates muscle tone, reducing tension. The dietary supplements generally include between about 0.01 wt % to about 1 wt %, and/or about 0.05 wt % to about 0.5 wt %, for example, about 0.075 wt % to 0.1 wt % of GABA, based on the total weight of the dietary supplement. When the dietary supplements of the invention are administered in a serving size of about one fluid ounce, the dietary supplements typically include between about 1 milligrams to about 300 milligrams, about 5 milligrams to about 100 milligrams, and/or between about 10 milligrams to about 75 milligrams, for example, about 15 milligrams to about 50 milligrams of GABA.

The dietary supplements of the invention include valerian root extract product. The valerian plant (*Valerian officinalis*) has been used as a medicinal herb for centuries. Valerian root extract product has historically been administered as a sleeping aid and to reduce anxiety. Valerian root extract product causes the release of GABA and inhibits the action of GABA transaminase, the enzyme that destroys the neurotransmitter. The inventors have also unexpectedly found that in combination with the other ingredients of the dietary supplements according to the invention, valerian root extract product provides energy without jitters and reduces stress. As used herein, an "extract product" is any compound, any agent, or mixtures thereof (including but not limited to an extract of plant material) that are derived from plant material. The term "plant material" refers to any component(s) of a plant including, for example, the leaves, flowers, fruit, stems, roots, seeds, and combinations thereof. When describing the specific exemplary amounts of extract products included in the dietary supplements according to the invention, carriers and/or diluents have been excluded. The dietary supplements generally include between about 0.01 wt % to about 1 wt %, 0.02 wt % to about 0.7 wt %, and/or about 0.03 wt % to about 0.5 wt %, for example, about 0.03 wt % to about 0.05 wt % of valerian root extract product, based on the total weight of the dietary supplement. When the dietary supplements of the invention are administered in a serving size of about one fluid ounce, the dietary supplements typically include between about 2 milligrams to about 300 milligrams, between about 5 milligrams to about 100 milligrams, between about 7.5 milligrams to about 25 milligrams, for example, about 10 milligrams to about 20 milligrams of valerian root extract product.

Both GABA and valerian root extract product are known to have sedative effects. Surprisingly, in the dietary supplements of the invention, GABA and valerian root extract product are included in amounts such that the dietary supplements provide stress relief without inducing lethargy. Because of the combination of GABA and valerian root extract product with other active ingredients in the dietary supplements according to the invention, the dietary supplements surprisingly and unexpectedly create a sense of calm while also enhancing energy and improving mental focus, resulting in a state of alert relaxation.

In a refinement, the dietary supplements of the invention may further include B vitamins. B vitamins are essential for the production of energy. B vitamins increase metabolism and also improve the functioning of the nervous system. Examples of B vitamins that may be included in the dietary supplements of the invention include, but are not limited to, Vitamin B1, Vitamin B2, Vitamin B5, Vitamin B6, Vitamin B7, Vitamin B9, and Vitamin B12. Most typically, the dietary supplements are substantially free of niacin (Vitamin B3), as previously described. B vitamins can be obtained from, for example, whole grains, potatoes, bananas, and beans.

For example, the dietary supplement may include Vitamin B6, also known as pyroxidine. Vitamin B6 is involved in over 100 metabolic reactions, including many relating to protein metabolism that increase energy. Vitamin B6 is also needed for the synthesis of neutrotransmitters important for mental clarity. Vitamin B6 can be found in, for example, fish, beef, poultry, and starchy vegetables. The dietary supplement may include between about 0.001 wt % to about 0.1 wt %, and/or between about 0.005 wt % to 0.05 wt %, for example between about 0.0075 wt % to about 0.025 wt % of Vitamin B6, based on the total weight of the dietary supplement. When the dietary supplements of the invention are administered in a serving size of about one fluid ounce, the dietary supplements typically include between about 0.2 milligrams to about 30 milligrams, and/or between about 1 milligrams to about 15 milligrams, for example, about 2 milligrams to about 6 milligrams of Vitamin B6.

In another example, the dietary supplement may include Vitamin B12, also known as cyanocobalamin. Vitamin B12 is essential for energy production and cellular metabolism. Vitamin B12 assists in the formation of amino acids and the conversion of carbohydrates to energy. Vitamin B12 also improves memory and optimal brain function. Vitamin B12 can be found in, for example, meat, fish, and dairy products. The dietary supplement may include between about 0.0001 wt % to about 0.01 wt %, and/or between about 0.0002 wt % to about 0.001 wt %, for example, about 0.0003 wt % to about 0.0005 wt % of Vitamin B12, based on the total weight of the dietary supplement. When the dietary supplements of the invention are administered in a serving size of about one fluid ounce, the dietary supplements typically include between about 0.02 milligrams to about 3 milligrams, about 0.03 milligrams to about 1 milligram, and/or between about 0.05 milligrams to about 0.75 milligrams, for example, about 0.05 milligrams to about 0.20 milligrams of Vitamin B12.

In addition to B vitamins, the dietary supplements may further include coenzyme Q10. Coenzyme Q10 is a powerful antioxidant that is essential for the production of energy by cells. Coenzyme Q10 also enhances brain function. The dietary supplements may include between about 0.01 wt % to about 1 wt %, between about 0.02 wt % to about 0.1 wt %, between about 0.025 wt % to about 0.05 wt %, for example, about 0.03 wt % to about 0.04 wt % of coenzyme Q10, based on the total weight of the dietary supplement. When the dietary supplements of the invention are administered in a serving size of about one fluid ounce, the dietary supplements typically include between about 2 milligrams to about 250 milligrams, and/or between about 5 milligrams to about 100 milligrams, for example, about 7.5 milligrams to about 12.5 milligrams of coenzyme Q10.

In one aspect, the dietary supplements of the invention may further include amino acids. Amino acids are used to synthesize proteins and other biomolecules and are essential for metabolism. Examples of amino acids include, but are not limited to, taurine, L-carnitine, acetyl L-carnitine, and L-theanine.

For example, the dietary supplements of the invention may further include taurine. Taurine is important in digestion and the processing of minerals and also enhances energy. Taurine is needed for proper muscle function and improves endurance. Taurine also reduces the accumulation and toxic effects of amyloid beta proteins in the brain, improving brain function. Taurine can be found in, for example, seafood and meat. The dietary supplements may include between about 0.1 wt % to about 5 wt %, and/or between about 0.5 wt % to about 2 wt %, for example, about 0.6 wt % to about 0.8 wt % of taurine, based on the total weight of the dietary supplement. When the dietary supplements of the invention are administered in a serving size of about one fluid ounce, the dietary supplements typically include between about 25 milligrams to about 1000 milligrams, and/or between about 100 milligrams to about 500 milligrams, for example, about 150 milligrams to about 250 milligrams of taurine.

In another example, the dietary supplements may include L-carnitine. L-carnitine plays a vital role in the transport of fats into mitochondria to produce energy. L-carnitine prevents the accumulation of toxins within cells and reduces physical fatigue. L-carnitine is also important in the production of acetylcholine, a neurotransmitter that is key to memory, intelligence, and mood. L-carnitine can be found in, for example, fish, milk, and poultry. The dietary supplements may include between about 0.1 wt % to about 5 wt %, and/or between about 0.2 wt % to about 2 wt %, for example, about 0.3 wt % to about 0.4 wt % of L-carnitine, based on the total weight of the dietary supplement. When the dietary supplements of the invention are administered in a serving size of about one fluid ounce, the dietary supplements typically include between about 25 milligrams to about 1000 milligrams, and/or between about 50 milligrams to about 500 milligrams, for example, about 75 milligrams to about 125 milligrams of L-carnitine.

In a further example, the dietary supplements may include acetyl L-carnitine. Acetyl L-carnitine transports fatty acids essential for the production of energy. Acetyl L-carnitine crosses the blood-brain barrier and is important for brain bioenergetics. The dietary supplements may include between about 0.01 wt % to about 1 wt %, and/or between about 0.05 wt % to about 0.5 wt %, for example about 0.075 wt % to about 0.15 wt % of acetyl L-carnitine, based on the total weight of the dietary supplement. When the dietary supplements of the invention are administered in a serving size of about one fluid ounce, the dietary supplements typically include between about 2 milligrams to about 300 milligrams, and/or between about 10 milligrams to about 100 milligrams, for example, about 20 milligrams to about 30 milligrams of acetyl L-carnitine.

In a final example, the dietary supplements may include L-theanine. L-theanine increases mental alertness and stimulates the production of alpha waves in the brain, which provide the optimal conditions for learning. L-theanine has neuroprotective properties against amyloid beta protein induced damage and can preserve peak brain function. L-theanine also increases relaxation and aids in the formation of GABA. L-theanine can be found in, for example, green tea and mushrooms. The dietary supplements may include between about 0.01 wt % to about 5 wt %, and/or between about 0.1 wt % to about 1 wt %, for example, about 0.15 wt % to about 0.20 wt % of L-theanine, based on the total weight of the dietary supplement. When the dietary supplements of the invention are administered in a serving size of about one fluid ounce, the dietary supplements typically include between about 2 milligrams to about 1000 milligrams, and/or between about 10 milligrams to about 100 milligrams, for example, about 30 milligrams to about 70 milligrams of L-theanine.

The dietary supplements of the invention may further comprise one or more additional ingredients to improve mental focus. Examples of additional ingredients that may be included in the dietary supplements of the invention in order to improve mental focus include, but are not limited to, choline bitartrate, inositol, alpha-glyceryl phosphoryl choline, and phosphatidyl serine.

For example, the dietary supplements may include choline bitartrate. Choline bitartrate is an essential nutrient that is needed for the manufacture of the acetylcholine. By supporting acetylcholine production, choline bitartrate improves focus and concentration. The dietary supplements may include between about 0.1 wt % to about 5 wt %, and/or between about 0.2 wt % to about 1 wt %, for example, about 0.3 wt % to about 0.7 wt % of choline bitartrate, based on the total weight of the dietary supplement. When the dietary supplements of the invention are administered in a serving size of about one fluid ounce, the dietary supplements typically include between about 25 milligrams to about 1000 milligrams, and/or between about 50 milligrams to about 500 milligrams, for example, about 100 milligrams to about 200 milligrams of choline bitartrate.

In another example, the dietary supplements of the invention may further include inositol. Inositol aids in the action of the neurotransmitter serotonin, which is known to promote feelings of well-being. Inositol can be found in, for example, cantaloupes, oranges, and other fruit. The dietary supplements may include between about 0.1 wt % to about 5 wt %, and/or between about 0.2 wt % to about 2 wt %, for example, about 0.25 wt % to about 0.50 wt % of inositol, based on the total weight of the dietary supplement. When the dietary supplements of the invention are administered in a serving size of about one fluid ounce, the dietary supplements typically include between about 25 milligrams to about 1000 milligrams, and/or between about 50 milligrams to about 200 milligrams, for example, about 75 milligrams to about 125 milligrams of inositol.

In a further example, the dietary supplements may include alpha-glyceryl phosphoryl choline (A-GPC). A-GPC contains the brain-boosting nutrient choline and can improve memory, thinking, and learning. The dietary supplements may include between about 0.01 wt % to about 1 wt %, and/or between about 0.02 wt % to about 0.5 wt %, for example, about 0.025 wt % to about 0.075 wt % of A-GPC, based on the total weight of the dietary supplement. When the dietary supplements of the invention are administered in a serving size of about one fluid ounce, the dietary supplements typically include between about 2 milligrams to about 250 milligrams, and/or between about 5 milligrams to about 100 milligrams, for example, about 10 milligrams to about 20 milligrams of A-GPC. A suitable commercially available supplement containing A-GPC is AlphaSize® (Chemi Nutra).

In a final example, the dietary supplements of the invention may further include phosphatidyl serine (PS). PS supports neuron generation and boosts blood flow to the brain. The compound plays a pivotal role in cerebral nerve transmission. The dietary supplements may include between about 0.01 wt % to about 1 wt %, and/or about 0.02 wt % to about 0.1 wt %, for example, about 0.025 wt % to about 0.075 wt % of PS, based on the total weight of the dietary supplement. When the dietary supplements of the invention are administered in a serving size of about one fluid ounce, the dietary supplements typically include between about 2 milligrams to about 250 milligrams, and/or between about 5 milligrams to about 25 milligrams, for example, about 7.5 milligrams to 12.5 milligrams of PS. A suitable commercially available source of PS is Sharp PS® Green (Enzymotec Ltd.).

The dietary supplements of the invention may further include one or more extract products. As used mentioned above, an "extract product" is any compound, any agent, or mixtures thereof (including but not limited to an extract of plant material) that are derived from plant material. The term "plant material" refers to any component(s) of a plant including, for example, the leaves, flowers, fruit, stems, roots, seeds, and combinations thereof. The dietary supplements may include extract products that are natural sources of energy and stress relief. Examples of extract products include, but are not limited to, gingko biloba extract product, citrus extract product, blueberry leaf extract product, turmeric root extract product, grape seed extract product, periwinkle extract product, wild green oat extract product, and huperzine A extract product. When describing the specific exemplary amounts of extract products included in the dietary supplements according to the invention, carriers and/or diluents have been excluded.

For example, the dietary supplements may further include gingko biloba (*Salisbura adiantifolia*) extract product. Gingko biloba extract product increases blood flow to the brain, strengthens brain cells and increases neurotransmission. Gingko biloba extract product improves cognitive performance and also increases muscle tone. The dietary supplements may include between about 0.01 wt % to about 1 wt %, and/or about 0.02 wt % to about 0.1 wt %, for example, about 0.025 wt % to about 0.075 wt % of gingko biloba extract product, based on the total weight of the dietary supplement. When the dietary supplements of the invention are administered in a serving size of about one fluid ounce, the dietary supplements typically include about 2 milligrams to about 250 milligrams, and/or between about 5 milligrams to about 25 milligrams, for example, about 7.5 milligrams to 12.5 milligrams of gingko biloba extract product.

In another example, the dietary supplements may include citrus extract product. Citrus extract product relieves stress and reduces inflammation caused by stress. The dietary supplements may include between about 0.01 wt % to about 1 wt %, and/or between about 0.02 wt % to about 0.5 wt %, for example, about 0.05 wt % to about 0.15 wt % of citrus extract product, based on the total weight of the dietary supplement. When the dietary supplements of the invention are administered in a serving size of about one fluid ounce, the dietary supplements typically include between about 2 milligrams to about 250 milligrams, and/or between about 10 milligrams to about 50 milligrams, for example, about 15 milligrams to about 25 milligrams of citrus extract product. A suitable commercially available source of citrus extract product is Serenzo™ (Bio Serae Laboratories S.A.S.).

In a further example, the dietary supplements of the invention may include blueberry leaf (*Vaccinium myrtillus* L.) extract product. Blueberry leaf extract product improves memory by aiding brain receptor sensitivity and reducing signal transduction deficits. The dietary supplements may include between about 0.01 wt % to about 5 wt %, and/or between about 0.025 wt % to about 1 wt %, for example, about 0.05 wt % to about 0.15 wt % of blueberry leaf extract product, based on the total weight of the dietary supplement. When the dietary supplements of the invention are administered in a serving size of about one fluid ounce, the dietary supplements typically include between about 2 milligrams to about 1000 milligrams, and/or between about 20 milligrams to about 100 milligrams, for example, about 15 milligrams to about 30 milligrams of blueberry leaf extract product.

The dietary supplements may further include turmeric root extract product (*Curcuma longa*). Turmeric root extract product has anti-inflammatory properties and provides pain relief to ease physical fatigue. Turmeric root extract product improves blood circulation by helping prevent platelet aggregation. The dietary supplements may include between about 0.01 wt % to about 1 wt %, between about 0.05 wt % to about 0.5 wt %, for example, about 0.075 wt % to about 0.15 wt % of turmeric root extract product, based on the total weight of the dietary supplement. When the dietary supplements of the invention are administered in a serving size of about one fluid ounce, the dietary supplements typically include between about 2 milligrams to about 250 milligrams, and/or between about 10 milligrams to about 50 milligrams, for example, about 15 milligrams to about 30 milligrams of turmeric root extract product. A suitable commercially available supplement containing turmeric root extract product is Curcumin C3 Complex® (Sabinsa Corp.)

The dietary supplements may further include grape seed (*Vitis vinifera*) extract product. Grape seed extract product is an antioxidant that can lower blood pressure. Grape Seed Extract product has been shown to reduce age-related oxidative damage and promotes cognitive performance. The dietary supplements may include between about 0.01 wt % to about 5 wt %, and/or between about 0.025 wt % to about 0.5 wt %, for example, about 0.05 wt % to about 0.15 wt % of grape seed extract product, based on the total weight of the dietary supplement. When the dietary supplements of the invention are administered in a serving size of about one fluid ounce, the dietary supplements typically include between about 2 milligrams to about 1000 milligrams, and/or between about 10 milligrams to about 100 milligrams, for example, about 15 milligrams to about 30 milligrams of grape seed extract product. A suitable commercially available supplement containing grape seed extract product is ActiVin® (Dry Creek Nutrition, Inc.).

The dietary supplements may further include periwinkle (*Vinca minor* L.) extract product. Periwinkle extract product enhances memory and increases blood flow in the brain and energy available to neurons. Periwinkle extract product also enhances metabolic reactions in the brain. The dietary supplements may include between about 0.01 wt % to about 1 wt %, and/or between about 0.025 wt % to about 0.5 wt %, for example, about 0.05 wt % to about 0.15 wt % of periwinkle extract product, based on the total weight of the dietary supplement. When the dietary supplements of the invention are administered in a serving size of about one fluid ounce, the dietary supplements typically include between about 2 milligrams to about 250 milligrams, and/or between about 10 milligrams to about 100 milligrams, for example, about 15 milligrams to about 30 milligrams of periwinkle extract product.

The dietary supplements may further include wild green oat extract product. Wild green oat extract product improves overall mental fitness and supports cognitive performance under stress. The botanical has been shown to improve attention, concentration, and focus. The dietary supplements may include between about 0.01 wt % to about 1 wt %, and/or between about 0.015 wt % to about 0.5 wt %, for example, about 0.02 wt % to about 0.03 wt % of wild green oat extract product, based on the total weight of the dietary supplement. When the dietary supplements of the invention are administered in a serving size of about one fluid ounce, the dietary supplements typically include between about 2 milligrams to about 250 milligrams, and/or between about 2.5 milligrams to about 50 milligrams, for example, about 5 milligrams to 10 milligrams of wild green oat extract product. A suitable commercially available supplement containing wild green oat extract product is Neuravena® (Frutarom).

In a final example, the dietary supplements of the invention may further include huperzine A extract product. Huperzine A extract product inhibits acetylcholinesterase and thus prevents the breakdown of acetylcholine. When the dietary supplements of the invention are administered in a serving size of about one fluid ounce, the dietary supplements typically include between about 0.0001 milligrams to about 0.5 milligrams, and/or between about 0.001 milligrams to about 0.05 milligrams, for example, about 0.0015 milligrams to about 0.0025 milligrams of huperzine A extract product. A suitable commercially available supplement of huperzine A extract product is Memorzine™ (Pharma Science Nutrients, Inc.).

The dietary supplements may further include ingredients to improve palatability. For example, the dietary supplements may include natural and artificial flavoring agents. Examples of flavoring agents include, but are not limited to, almond, apple, berry, caramel, citrus, cherry, chocolate, coconut, grape, green tea, honey, lemon, lime, mango, mint, oatmeal, orange, peach, peanut, pineapple, raisin, vanilla, and combinations thereof. The dietary supplements may include between about 1 wt % to about 10 wt %, and/or between about 1.5 wt % to about 5 wt %, for example, about 2 wt % of flavoring agents, based on the total weight of the dietary supplement. When the dietary supplements of the invention are administered in a serving size of about one fluid ounce, the dietary supplements typically include between about 200 milligrams to about 2500 milligrams, and/or between about 300 milligrams to about 1000 milligrams, for example, about 300 milligrams to about 500 milligrams of flavoring agents.

In another example, the dietary supplements may include malic acid. Malic acid provides a tart flavor. The dietary supplements may include between about 0.1 wt % to about 5 wt %, and/or between about 0.2 wt % to about 2 wt %, for example, about 0.25 wt % to about 0.50 wt % of malic acid, based on the total weight of the dietary supplement. When the dietary supplements of the invention are administered in a serving size of about one fluid ounce, the dietary supplements typically include between about 25 milligrams to about 1000 milligrams, and/or between about 50 milligrams to about 500 milligrams, for example, about 75 milligrams to 125 milligrams of malic acid.

In the methods according to the invention, the dietary supplements may be administered to a subject to increase energy and mental focus and reduce stress. In a preferred aspect, the dietary supplements may be administered in liquid form as a drink. A single serving of a dietary supplement of the invention may comprise about one fluid ounce, as previously defined. Table 1 shows the composition per serving of a representative dietary supplement in accordance with the invention. In one aspect, the dietary supplements are administered daily. The dietary supplements may also be administered ad libitum. The dietary supplements may also contain about 5 calories and 1 gram of total carbohydrates per serving. The dietary supplements may be packaged in individual bottles containing one to two servings, or in larger vessels containing multiple servings. In one aspect, up to three servings of the dietary supplements are self-administered by a subject per day. Advantageously, the dietary supplements in accordance with the invention do not require refrigeration.

As described throughout the present disclosure, the caffeine-free dietary supplements of the invention and methods of administering the same advantageously provide a natural and safe increase in energy while also improving mental focus and reducing stress in a subject. Accordingly, the dietary supplements may be administered according to the methods of the invention whenever a subject is in need of increased energy, mental focus and/or reduced stress. For example, the dietary supplements may be administered in the morning to provide an energetic start to the day. The dietary supplements may also be administered in the afternoon to mitigate a midday dip in energy. Additionally, the dietary supplements may be administered prior to physical activity to boost athletic performance and endurance. Furthermore, the dietary supplements may be administered while at work or school to improve concentration and allow a subject to skillfully handle assignments. In yet another example, the dietary supplements may also be administered while driving to allow one to keep focused and alert when traveling.

TABLE 1

Composition of a Representative Dietary Supplement in Accordance with the Invention

| Ingredient | Milligrams Per Serving (One Fluid Ounce) |
| --- | --- |
| Purified Water | balance |
| Flavoring Agents | about 300 to 500 |
| Beta Alanine | about 200 to 400 |
| Taurine | about 150 to 250 |
| Natural Sweetening Agents | about 120 to 250 |
| Choline Bitartrate | about 100 to 200 |
| Fish Oil | about 50 to 200 |
| Malic Acid | about 75 to 125 |
| L-Carnitine | about 75 to 125 |
| Inositol | about 75 to 125 |
| L-Theanine | about 30 to 70 |
| Blueberry Leaf Extract Product 5:1 | about 15 to 30 |
| GABA | about 15 to 30 |
| Acetyl L-Carnitine | about 75 to 125 |
| Turmeric Root Extract Product | about 15 to 30 |
| Grape Seed Extract Product | about 15 to 30 |
| Periwinkle Extract Product | about 15 to 30 |
| Citrus Extract Product (Serenzo ™) | about 15 to 25 |
| Alpha-Glyceryl Phosphoryl Choline | about 10 to 20 |
| Valerian Root Extract Product 4:1 | about 10 to 20 |
| Gingko Biloba Extract Product 5:1 | about 7.5 to 12.5 |
| Phosphatidylserine | about 7.5 to 12.5 |
| Coenzyme Q10 | about 7.5 to 12.5 |
| Wild Green Oat Extract Product | about 5 to 10 |
| Vitamin B6 (Pyridoxine HCL) | about 2 to 6 |
| Resveratrol | about 2 to 5 |
| Vitamin B12 (Cyanocobalamin) | about 0.05 to 0.20 |
| Huperzine A Extract Product | about 0.0015 to 0.0025 |

What is claimed:

1. A method for increasing energy in a subject, the method comprising administering to a subject a dietary supplement comprising omega-3 fatty acids, resveratrol, beta alanine, gamma aminobutyric acid (GABA), and valerian root extract product, in amounts such that the dietary supplement is effective for increasing energy and mental focus and reducing stress in the subject, wherein the dietary supplement is substantially free of caffeine, wherein the energy of the subject is increased.

2. The method of claim 1, wherein the dietary supplement is substantially free of niacin.

3. The method of claim 1, wherein the dietary supplement is substantially free of artificial sweeteners.

4. The method of claim 1, wherein the dietary supplement further comprises B vitamins and coenzyme Q10.

5. The method of claim 1, wherein the dietary supplement further comprises one or more amino acids selected from the group consisting of taurine, L-carnitine, acetyl L-carnitine, and L-theanine.

6. The method of claim 1, wherein the dietary supplement further comprises one or more ingredients to improve mental focus selected from the group consisting of choline bitartrate, inositol, alpha-glyceryl phosphoryl choline, and phosphatidyl serine.

7. The method of claim 1, wherein the dietary supplement further comprises one or more extract products selected from the group consisting of gingko biloba extract product, citrus extract product, blueberry leaf extract product, turmeric root extract product, grape seed extract product, periwinkle extract product, wild green oat extract product, and huperzine A extract product.

8. The method of claim 1, wherein the dietary supplement further comprises one or more of natural flavoring agents, artificial flavoring agents, malic acid, and sweetening agents.

9. The method of claim 1, comprising administering the dietary supplement to the subject daily.

10. The method of claim 4, wherein the dietary supplement comprises about 0.01 weight percent (wt %) to about 5 wt % omega-3 fatty acids, about 0.001 wt % to about 1 wt % resveratrol, about 0.1 wt % to about 10 wt % beta alanine, about 0.01 wt % to about 1 wt % GABA, about 0.01 wt % to about 1 wt % valerian root extract product, about 0.001 wt % to about 0.1 wt % Vitamin B6, about 0.0001 wt % to about 0.01 wt % Vitamin B12, and about 0.01 wt % to about 1 wt % coenzyme Q10, based on the total weight of the dietary supplement.

11. The method of claim 4, comprising administering a serving comprising about one fluid ounce of the dietary supplement to the subject daily, wherein the dietary supplement comprises omega-3 fatty acids in a range of about 5 milligrams to about 1000 milligrams, resveratrol in a range of about 0.1 milligrams to about 250 milligrams, beta alanine in a range of about 25 milligrams to about 3000 milligrams, GABA in a range of about 1 milligram to about 300 milligrams, valerian root extract product in a range of about 2 milligrams to about 300 milligrams, Vitamin B6 in a range of about 0.02 milligrams to about 30 milligrams, Vitamin B12 in a range of 0.02 milligrams to about 3 milligrams, and coenzyme Q10 in a range of about 2 milligrams to about 250 milligrams per serving.

12. A dietary supplement for increasing energy comprising omega-3 fatty acids, resveratrol, beta alanine, GABA, and valerian root extract product, in amounts such that the dietary supplement is effective for increasing energy and mental focus and relieving stress in a subject, wherein the dietary supplement is substantially free of caffeine.

13. The dietary supplement of claim 12, wherein the dietary supplement is substantially free of niacin.

14. The dietary supplement of claim 12, wherein the dietary supplement is substantially free of artificial sweeteners.

15. The dietary supplement of claim 12, further comprising B vitamins and coenzyme Q10.

16. The dietary supplement of claim 12, further comprising one or more amino acids selected from the group consisting of taurine, L-carnitine, acetyl L-carnitine, and L-theanine.

17. The dietary supplement of claim 12, further comprising one or more ingredients to improve mental focus selected from the group consisting of choline bitartrate, inositol, alpha-glyceryl phosphoryl choline, and phosphatidyl serine.

18. The dietary supplement of claim 12, further comprising one or more extract products selected from the group consisting of gingko biloba extract product, citrus extract product, blueberry leaf extract product, turmeric root extract product, grape seed extract product, periwinkle extract product, wild green oat extract product, and huperzine A extract product.

19. The dietary supplement of claim 12, further comprising one or more of natural flavoring agents, artificial flavoring agents, malic acid, and sweetening agents.

20. The dietary supplement of claim 15, wherein the dietary supplement comprises about 0.01 weight percent (wt %) to about 5 wt % omega-3 fatty acids, about 0.001 wt % to about 1 wt % resveratrol, about 0.1 wt % to about 10 wt % beta alanine, about 0.01 wt % to about 1 wt % GABA, about 0.01 wt % to about 1 wt % valerian root extract product, about 0.001 wt % to about 0.1 wt % Vitamin B6, about 0.0001 wt % to about 0.01 wt % Vitamin B12, and about 0.01 wt % to about 1 wt % coenzyme Q10, based on the total weight of the dietary supplement.

21. The dietary supplement of claim 15, wherein a serving of the dietary supplement has a volume of about one fluid ounce and comprises omega-3 fatty acids in a range of about 5 milligrams to about 1000 milligrams, resveratrol in a range of about 0.1 milligrams to about 250 milligrams, beta alanine in a range of about 25 milligrams to about 3000 milligrams, GABA in a range of about 1 milligram to about 300 milligrams, valerian root extract product in a range of about 2 milligrams to about 300 milligrams, Vitamin B6 in a range of about 0.02 milligrams to about 30 milligrams, Vitamin B12 in a range of 0.02 milligrams to about 3 milligrams, and coenzyme Q10 in a range of about 2 milligrams to about 250 milligrams per serving.

* * * * *